(12) United States Patent
Mirza et al.

(10) Patent No.: US 11,096,710 B2
(45) Date of Patent: **\*Aug. 24, 2021**

(54) COMPACT ENDOSCOPIC SURGICAL BLADE ASSEMBLY AND METHOD OF USE THEREOF

(75) Inventors: Romi Mirza, Smithtown, NY (US); Ather Mirza, Smithtown, NY (US)

(73) Assignee: A.M. Surgical, Inc., Smithtown, NY (US)

(\*) Notice: Subject to any disclaimer, the term of this patent is extended or adjusted under 35 U.S.C. 154(b) by 0 days.

This patent is subject to a terminal disclaimer.

(21) Appl. No.: 13/602,968

(22) Filed: Sep. 4, 2012

(65) Prior Publication Data

US 2014/0066963 A1   Mar. 6, 2014

(51) Int. Cl.
*A61B 17/32*   (2006.01)

(52) U.S. Cl.
CPC ........... *A61B 17/320036* (2013.01); *A61B 17/320016* (2013.01)

(58) Field of Classification Search
CPC ........ A61B 17/320016; A61B 17/3213; A61B 17/295; A61B 17/285; A61B 17/32113; A61B 17/3211; A61B 17/320036; A61B 17/32; A61B 2017/32004
USPC ......... 606/167, 171–172, 170, 169; 600/104, 600/562, 563; 30/160–163
See application file for complete search history.

(56) References Cited

U.S. PATENT DOCUMENTS

| | | | |
|---|---|---|---|
| 5,273,024 A | 12/1993 | Menon et al. | |
| 5,322,055 A | 6/1994 | Davison et al. | |
| 5,447,513 A | 9/1995 | Davison et al. | |
| 5,569,283 A | 10/1996 | Green et al. | |
| 5,571,127 A * | 11/1996 | DeCampli | A61B 17/3211 30/125 |
| 5,595,410 A * | 1/1997 | Wilson et al. | 292/306 |
| 5,755,713 A * | 5/1998 | Bilof et al. | 606/1 |
| 6,093,154 A * | 7/2000 | Burek | A61B 90/39 600/564 |
| 6,589,231 B1 | 7/2003 | Gobron et al. | |
| 2004/0098005 A1 | 5/2004 | Mirza et al. | |
| 2004/0230155 A1 | 11/2004 | Blanco et al. | |

(Continued)

FOREIGN PATENT DOCUMENTS

WO   2012/096746 A1   7/2012

OTHER PUBLICATIONS

International Search Report and Written Opinion issued in International Patent Application No. PCT/US2013/057339 dated Nov. 19, 2013.

(Continued)

*Primary Examiner* — Erich G Herbermann
(74) *Attorney, Agent, or Firm* — Bodner & O'Rourke, LLP; Gerald T. Bodner; Christian P. Bodner

(57) ABSTRACT

An endoscopic surgical device comprising a slotted clear cannula, a blade and a case, wherein the cannula is attached to the case, and wherein the blade is enclosed in the case and is slidable into the cannula is disclosed. The blade is enclosed within the case and cannula, and has a horizontally-oriented pushing component and a vertically-oriented cutting component that protrudes through the slot of the cannula. A method for a performing an operative procedure on a target tissue in a subject using the endoscopic surgical device is also described.

9 Claims, 8 Drawing Sheets

(56) References Cited

U.S. PATENT DOCUMENTS

| | | | |
|---|---|---|---|
| 2007/0288043 A1* | 12/2007 | Rehnke | A61B 17/320036 606/170 |
| 2008/0045989 A1 | 2/2008 | Welborn | |
| 2008/0065124 A1* | 3/2008 | Olson | 606/159 |
| 2008/0195128 A1* | 8/2008 | Orbay | A61B 1/00048 606/170 |
| 2010/0069936 A1* | 3/2010 | Palmer et al. | 606/167 |
| 2010/0168773 A1* | 7/2010 | Funderburk | A61B 17/3213 606/167 |
| 2010/0228083 A1 | 9/2010 | Mirza et al. | |
| 2010/0228085 A1 | 9/2010 | Mirza et al. | |
| 2011/0046710 A1* | 2/2011 | Mangiardi et al. | 623/1.11 |
| 2013/0296922 A1* | 11/2013 | Allen, IV | A61B 18/1445 606/205 |

OTHER PUBLICATIONS

Supplementary Partial European Search Report of EP Application No. 13766220.1 dated Feb. 12, 2015.
International Preliminary Report on Patentability and Written Opinion of the International Searching Authority of International Application No. PCT/US2013/029831 dated Mar. 19, 2015.

* cited by examiner

COMPACT ENDOSCOPIC SURGICAL BLADE ASSEMBLY AND METHOD OF USE THEREOF

FIELD

This application generally relates to medical devices. In particular, the application relates to devices and methods for endoscopic surgery, e.g., for endoscopic tunnel or pulley release surgery.

BACKGROUND

Endoscopic surgery is a minimally invasive surgical procedure that is performed through small incisions or natural body openings. An endoscopic procedure typically involves use of specialized devices and remote-control manipulation of instruments with indirect observation of the surgical field through an endoscope or similar device. Comparing to open surgery, endoscopic surgery may result in shorter hospital stays, or allow outpatient treatment.

Trigger finger is characterized by catching, snapping or locking of the involved finger flexor tendon, associated with dysfunction and pain. Localized inflammation or nodular swelling of said flexor tendon causes a disparity in size between the flexor tendon and the surrounding retinacular pulley system, most commonly at the level of the first annular (A1) pulley. When the subject extends the involved finger, the tendon will "catch" on the pulley, followed by an abrupt popping of the tendon through the pulley. This results in a difficulty flexing or extending the finger and the "triggering" phenomenon. Typically, a first course of treatment for trigger finger is corticosteroid injections into the tendon sheath to reduce inflammation. When corticosteroid injection is not or no longer effective, surgical division of the A1 pulley is indicated.

Carpal tunnel syndrome is an entrapment median neuropathy resulting from compression of the median nerve at the wrist in the carpal tunnel. Symptoms of carpal tunnel syndrome include tingling, numbness, weakness, or pain felt in the fingers supplied by the median nerve or in the palm. Repetitive tasks, force, posture, and vibration have been cited as causative or contributing factors to carpal tunnel syndrome. Palliative treatments for carpal tunnel syndrome include direct corticosteroid injections, splinting, oral corticosteroids and/or behavior modification. Failure of these methods within a reasonable period of time, and/or the presence of other contributing factors, indicates a need for surgical division of the carpal tunnel.

Other conditions involving the compression of a nerve by a ligament pulley or tunnel include Guyon's tunnel (or canal) syndrome, which is a compression of the ulnar nerve as it passes through Guyon's tunnel at the wrist; cubital tunnel syndrome, which is a compression of the ulnar nerve as it passes through the cubital tunnel at the elbow; radial tunnel syndrome, which is a compression of the radial nerve as it travels from the brachial plexus to the wrist and hand; and pronater teres syndrome, which is a compression neuropathy of the median nerve in the region of the elbow.

Conventional surgical techniques and equipment for pulley or tunnel release require a fairly large incision over the pulley or tunnel and spreading of the incision to allow viewing and instrument access. These techniques can require a longer period of recovery than endoscopic methods and have greater levels of post-operative pain due to the incision size and level of manipulation during the procedure.

Typically, endoscopic surgery has involved a number of steps and separate devices for performing pulley or tunnel division. After making an incision and opening a path to the pulley or tunnel using a blunt instrument, a cannula is inserted into the path. Briefly, in order to smoothly insert the cannula, the central lumen of the cannula must be filled with a device, such as an obturator. The obturator is then removed and an endoscope is inserted into the cannula to view the pulley or tunnel. The endoscope is then withdrawn from the cannula, a knife is either advanced into the cannula for division or a specialized knife assembly is affixed to the endoscope and the knife/endoscope assembly is advanced into the cannula for division The present application fulfils a need in the art for a compact device for uniportal endoscopic pulley or tunnel release surgery that eliminates the need for a separate device, such as an obturator, for filling the cannula during insertion and eliminates the need to remove the endoscope in order to insert a blade or blade assembly.

SUMMARY

One aspect of the present application relates to an endoscopic surgical device comprising a slotted clear cannula, a blade and a case, wherein the cannula is attached to the case, and wherein the blade is enclosed in the case and is slidable into the cannula.

Another aspect of the present application relates to a slotted clear cannula that is closed at one end and open at the other, wherein the slot is contiguous with the open end of the cannula. In a further embodiment, the closed end of the cannula is tapered.

Another aspect of the present application relates to a kit comprising an endoscopic surgical device comprising a slotted clear cannula, a blade and a case, wherein the cannula is attached to the case, and further wherein the blade is enclosed in the case and is slidable into the cannula.

Another aspect of the present application relates to a method for a performing a uniportal endoscopic surgical procedure a target tissue in a subject in need thereof, comprising: establishing an entry portal in the subject, inserting into the entry portal the cannula of an endoscopic surgical device comprising a slotted clear cannula, a blade and a case, wherein the cannula is attached to the case, and further wherein the blade is enclosed in the case and is slidable into the cannula, and extending the cannula through the entry portal to the target tissue.

Another aspect of the present application relates to an endoscopic surgical device, comprising a slotted clear cannula, a scraper, a blade and a case, wherein, the cannula is attached to the case, in a pre-deployment configuration the scraper and the blade are enclosed in the case, the blade and scraper are individually selectable for deployment orientation, and in deployment orientation the blade or scraper are slidable into the cannula.

BRIEF DESCRIPTION OF THE DRAWINGS

The present invention can be better understood by reference to the following drawings. The drawings are merely exemplary to illustrate certain features that may be used singularly or in combination with other features and the present invention should not be limited to the embodiments shown.

DETAILED DESCRIPTION

Figure 1:
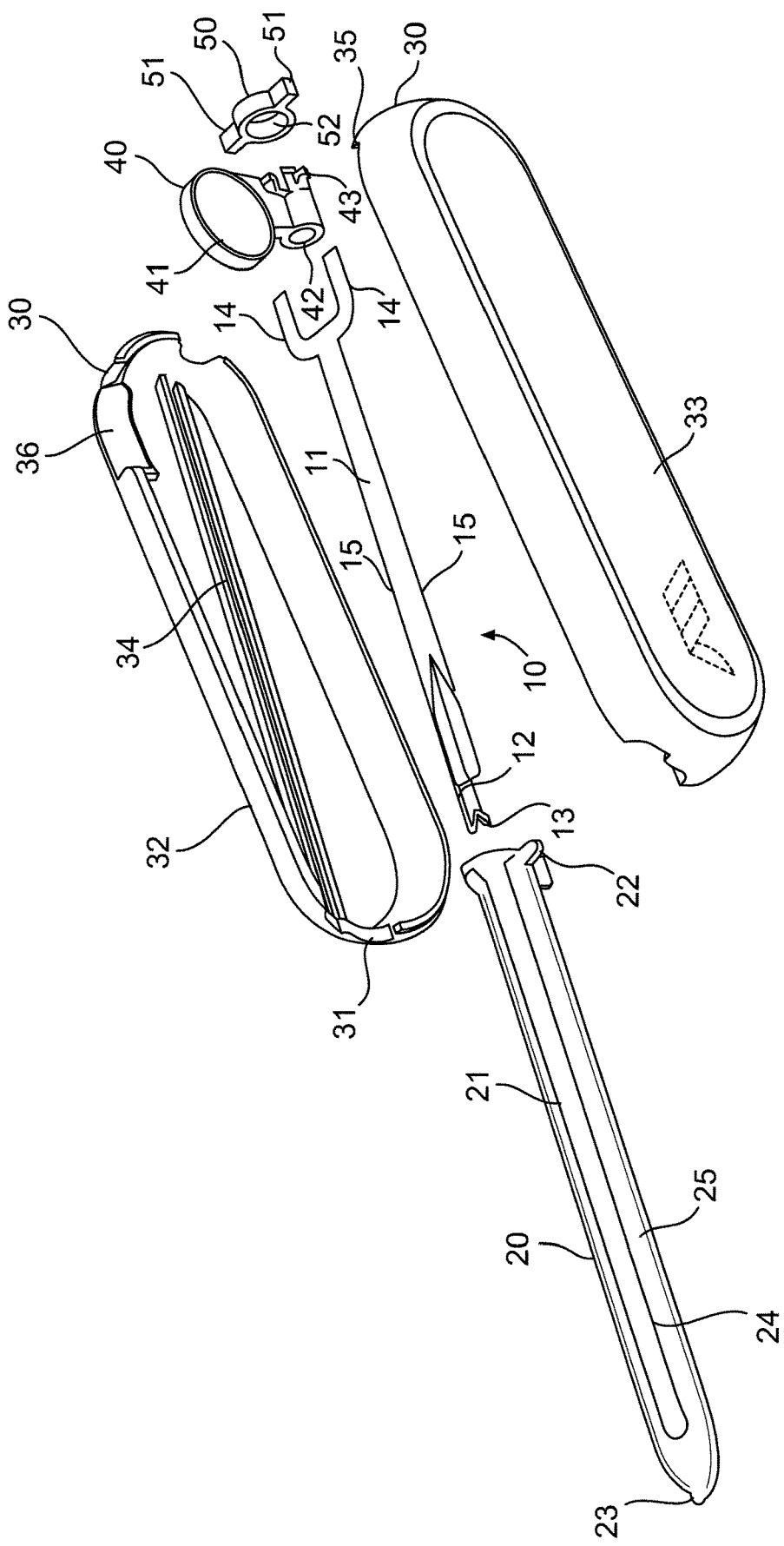
FIG. 1 is an exploded view of one embodiment of the device of the present application.

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. The present invention is not intended to be limited to the embodiments shown, but is to be accorded the widest possible scope consistent with the principles and features disclosed herein.

This description is intended to be read in connection with the accompanying drawings, which are to be considered part of the entire written description of this application. The drawing figures are not necessarily to scale and certain features of the application may be shown exaggerated in scale or in somewhat schematic form in the interest of clarity and conciseness. In the description, relative terms such as "front," "back," "up," "down," "top," "bottom," "upper," "lower," "distal," and "proximate" as well as derivatives thereof, should be construed to refer to the orientation as then described or as shown in the drawing figure under discussion. These relative terms are for convenience of description and normally are not intended to require a particular orientation. Terms concerning attachments, coupling and the like, such as "connected," "mounted," and "attached," refer to a relationship wherein structures are secured or attached to one another either directly or indirectly through intervening structures, as well as both movable or rigid attachments or relationships, unless expressly described otherwise.

The term "trigger finger," as used herein, also refers to "trigger digit," "trigger thumb," and "stenosing tendovaginitis."

As used herein, the terms "horizontal" and "vertical," and derivatives of those terms, are used in respect to their relationship to the plane defined by the slot in the cannula of the present application. "Vertical" refers to the plane that can, for example, pass through the slot of the cannula and bisect the cannula into two equal halves, while "horizontal" refers to a plane that is perpendicular to the vertical plane. The horizontal plane may be a level plane with respect to the length of the cannula or case of the device, or may be at an angle to that level plane, allowing some upward or downward movement of elements moving along the horizontal plane with respect to the level plane.

The present application describes a compact device for performing endoscopic surgical procedures, comprising a clear cannula that is attached to a case. The cannula has a closed distal end, allowing the cannula to be inserted through a portal (such as an incision) without the use of a cannula filling instrument, such as an obturator. The case further comprises a blade that extends into the cannula, and a paddle for pushing the blade. In some embodiments, the case further comprises a ring that secures the paddle to the case, but allows the paddle to rotate side-to-side. The present assembly provides a convenient means for performing endoscopic surgical procedures with the elimination of the steps of inserting an obturator into the cannula for introducing the cannula into a portal, removing the obturator from the cannula, and removing an endoscope from the cannula so that a blade can be inserted and advanced into the cannula. The preassembled nature of the device also provides convenience for the practitioner in that the cannula and blade are available in a single package that requires no further assembly and can be used easily in an office setting without the need for some traditional endoscopic equipment that may be too expensive or cumbersome to use outside of a hospital. Additionally, the present device also can be easily transported and used in remote settings, such as by emergency medical personnel, first responders or military medical personnel The use of the present device is exemplified in this application for, but not limited to, endoscopic surgical division of a pulley or tunnel. Some other non-limiting uses for the present device include, for example, other divisions or partial separation of a tendon or ligament, cutting, dividing, separating or making an incision in connective tissue, muscle, cartilage, membranes, skin, other body tissues or organs or any other use of the device that can be envisioned or carried out by the practitioner. As used herein, the term "practitioner" refers to one of skill in the art or any other user of the present device.

One aspect of the present application relates to an endoscopic surgical device comprising a slotted clear cannula, a blade and a case, wherein the cannula is attached to the case, and further wherein the blade is enclosed in the case and is slidable into the cannula.

In one embodiment, the end of the slotted clear cannula distal to the case is closed. In a further embodiment, the closed end of the cannula is tapered.

In another embodiment, the cannula further internally comprises horizontal blade guidance tracks below the slot. In a further embodiment, the cannula further internally comprises a channel below the horizontal blade guidance tracks.

In another embodiment, the blade comprises a vertically-oriented cutting surface and a horizontally-oriented pushing region. In a further embodiment, the blade is slidable within a cannula. In another further embodiment, the vertically-oriented cutting surface of the blade protrudes through the slot of a cannula. In still another further embodiment, the horizontally-oriented pushing region of the blade seats in comprises horizontal blade guidance tracks of a cannula.

In another embodiment, the blade comprises horizontal tabs at the end distal to the cutting surface.

In another embodiment, the case internally comprises horizontally opposed guidance slots. In a further embodiment, the horizontal tabs of the blade are slidably associated with the horizontally opposed guidance slots of the case.

In another embodiment, a pusher paddle is slidably associated with the case. In a further embodiment, the pusher paddle contacts the end of the blade distal to the cutting surface.

In another embodiment, sliding the pusher paddle in the direction of the cutting surface pushes the blade into the cannula and causes the cutting surface to at least partially protrude through the slot of the cannula.

In another embodiment, the device further comprises a retainer ring that attaches to the pusher paddle. In a further embodiment, the retainer ring allows the pusher paddle to rotate side-to-side. In another further embodiment, the retainer ring comprises wings. In a still further embodiment, the wings are slidably associated with the horizontally opposed guidance slots of the case.

In another embodiment, the case further comprises lateral slot. In a further embodiment, the pusher paddle protrudes through the lateral slot.

In another embodiment, the case comprises an opening in the proximal end of the case distal to the cannula. In a further embodiment, the opening is below the horizontally opposed guidance slots of the case. In a further embodiment, an endoscope is slidably insertable through the opening in the end of the case and into the channel of the clear cannula.

Another aspect of the present application relates to a slotted clear cannula that is closed at one end and open at the other, wherein the slot is contiguous with the open end of the cannula. In a further embodiment, the closed end of the cannula is tapered.

In one embodiment, the cannula comprises a channel for the insertion of an endoscope. In a further embodiment, the cannula further internally comprises horizontal blade guidance tracks below the slot. In a still further embodiment, the channel is below the horizontal blade guidance tracks.

Another aspect of the present application relates to a kit comprising an endoscopic surgical device comprising a slotted clear cannula, a blade and a case, wherein the cannula is attached to the case, and further wherein the blade is enclosed in the case and is slidable into the cannula.

In one embodiment, the kit further comprises an endoscope. In a further embodiment, the endoscope is slidably insertable through an opening in the 1 end of the case distal to the cannula and a the channel in the cannula.

In another embodiment, the kit further comprises a scalpel.

In yet another embodiment, the kit further comprises a blunt instrument for tissue separation. In a still further embodiment, the blunt instrument is an elevator.

Another aspect of the present application relates to a method for a performing a uniportal endoscopic surgical procedure on a target tissue in a subject in need thereof, comprising: establishing an entry portal in the subject, inserting into the entry portal the cannula of an endoscopic surgical device comprising a slotted clear cannula, a blade and a case, wherein the cannula is attached to the case, and further wherein the blade is enclosed in the case and is slidable into the cannula, and extending the cannula through the entry portal to the target tissue.

In a particular embodiment, the establishing an entry portal comprises making an incision.

In one embodiment, an arthroscope is inserted through the case and into the cannula to view the target tissue and the surrounding tissues, assuring that the slot of the cannula is in proper orientation to the target tissue.

In a further embodiment, the knife is advanced through the cannula so that the blade moves in contact with the target tissue through the slot, operatively engaging the target tissue with the blade. In a still further embodiment, the blade is further advanced through the cannula to divide the target tissue.

In one particular embodiment, the operative procedure is selected from the group consisting of trigger finger release, carpal tunnel release, cubital tunnel release, plantar fascia release, lateral release for patella realignment, release of the extensor tendons, release of the posterior or other compartments of the leg, and forearm fascial release.

In another particular embodiment, the target tissue is selected from the group consisting of the A1 pulley, carpal tunnel, cubital tunnel and Guyon's tunnel.

Another aspect of the present application relates to an endoscopic surgical device, comprising a slotted clear cannula, a scraper, a blade and a case, wherein, the cannula is attached to the case, in a pre-deployment configuration the scraper and the blade are enclosed in the case, the blade and scraper are individually selectable for deployment orientation, and in deployment orientation the blade or scraper are slidable into the cannula.

In one particular embodiment, the end of the slotted clear cannula distal to the case is closed. In a further embodiment, the closed end of the cannula is tapered.

In another embodiment, the cutting surface of the blade protrudes through the slot of the cannula.

In still another embodiment, the surface of the scraper protrudes through the slot of the cannula.

Linear Operated Device

FIG. 1 shows an exemplary device of the present application. The device comprises a blade 10, a slotted clear cannula 20, and a case 30. The device may further include a pusher paddle 40, and may still further include a retainer ring 50.

The blade 10 comprises a horizontally-oriented pushing component 11 and a vertically-oriented cutting component 12. The cutting component 12 further comprises a sharpened cutting surface 13 at the forward end, which is the end of the blade most proximal to the cannula 20 of the device. The cutting surface may be single-beveled or double-beveled.

In some embodiments, the cutting surface 13 of the blade is a single cutting surface. In some further embodiments, that single cutting surface is angled downward such that the upper end of the cutting surface is forward of the lower end of the cutting surface. In other further embodiments, that single cutting surface has a concave curve and is semi-circular or crescent shaped.

In other embodiments, the cutting surface 13 of the blade is divided into an upper cutting surface and a lower cutting surface that are at an angle to one another and meet at a central crotch.

The design of the present blade is such that it is usable in endoscopic surgery in a manner that allows the practitioner to extend the blade through the cannula to the target tissue without damage to surrounding tissue and/or organs. The blade is made from materials commonly used for surgical blades or scalpels, such materials include, but are not limited to, hardened and tempered steel, stainless steel, high carbon steel, titanium, alloys and ceramic.

In particular embodiments, the blade is made from stainless steel. In a further embodiment, the stainless steel is martensitic stainless steel. An exemplary martensitic stainless steel is Bohler-Uddeholm AEB-L martensitic stainless steel. In a still further embodiment, the martensitic stainless steel is heat-treated. In another further embodiment, the stainless steel is 440 A stainless steel. In a particular embodiment, the blade is made from Hitachi GIN-5 SST-MODIFIED 440-A stainless steel. The blade is optionally flash electropolished. The cutting edges are machine finished and must be sharp. In a particular embodiment, the steel of the blade is heat-treated to Rockwell C hardness of about 50-72. In a more particular embodiment, the steel of the blade is heat-treated to Rockwell C hardness of 58-64.

In particular embodiments, the entire blade 10 is cut from a single sheet of, or is cast from, a material commonly used for surgical blades or scalpels. The cutting component 12 is then bent into a vertical orientation that is perpendicular to the horizontal orientation of the pushing component 11. In some embodiments, the bevel(s) of the cutting surface 13 are ground prior to bending. In other embodiments, the bevel(s) of the cutting surface 13 are ground after bending.

In other embodiments, the pushing component 11 and cutting component 12 of the blade 10 are fabricated separately (by cutting or casting) and affixed to one another in their respective proper orientations. In some further embodiments, the pushing component 11 and cutting component 12 are fabricated from the same material. In other further embodiments, the pushing component 11 and cutting component 12 are fabricated from different materials, but at least the cutting component 12 is fabricated from a material commonly used for surgical blades or scalpels. In such a case, the pushing component 11 of the blade 10 may be fabricated from any suitable material providing adequate strength and rigidity for pushing the cutting component including, but not limited to, plastics, polycarbonate, hardened and tempered steel, stainless steel, high carbon steel, titanium, alloys and ceramic. Affixing of the cutting component 12 to the pushing component 11 may be accomplished by any means known in the art, such as the use of a suitable adhesive or by welding, including laser welding. In a particular embodiment, the strength of the bond between the pushing component 11 and the cutting component 12 is tested by applying torque to the unit, for example about 10 in-lbs of torque.

In particular embodiments, the blade 10 further comprises tabs 14 at the end of the pushing component 11 distal to the cutting component 12. In some embodiments, the tabs 14 extend outward to the sides of the blade 10 in the same horizontal plane as the pushing component 11, although in some embodiments, the tabs 14 may also be at an angle to that horizontal plane, as appropriate for the application. As used herein, the term "tabs" refers to either a single tab structure, two tab structures, or any other multiple as appropriate.

The tabs 14 are slidably engaged with the case 30 in a manner to be further described below.

The cannula 20 is made of a clear plastic material so that the entirety of the surrounding tissue can be viewed with an endoscope. The cannula 20 is slotted along its top, with the slot 21 being contiguous with the open end 22 that is proximal to the case 30. In some embodiments, the distal end 23 of the cannula 20 is closed, such that the cannula 20 can be inserted into a channel made through body tissue without the use of an obturator. In particular embodiments, the closed distal end 23 of the cannula is tapered, but is sufficiently blunted such that it does not damage bodily tissues as it is advanced though an incision and channel through bodily tissue, or through a natural body opening.

The cannula 20 engages with the blade 10 of the device such that the cutting component 12 inserts into and is slidably engaged with the slot 21.

In some embodiments, the cannula 20 further internally comprises horizontal blade guidance tracks 24 perpendicular to the plane of and below the slot 21. The sides 15 of the pushing component 11 of the blade 10 slidably engage with the horizontal blade guidance tracks 24, in order to allow the accurate advancement of the cutting component 12 of the blade 10 through the slot 21. In some further embodiments, the height of the horizontal blade guidance tracks 24 is level with respect to the distance from the slot 21, such that the distance the cutting surface 13 protrudes through the slot 21 is the same over the entire course of travel from the proximal end 22 of the cannula 20 to the distal end 23 of the cannula 20. In other further embodiments, the height of the horizontal blade guidance tracks 24 is at an angle with respect to the distance from the slot 21, such that the distance the cutting surface 13 protrudes through the slot 21 is lower at or near the proximal end 22 of the cannula 20 and higher at or near the distal end 23 of the cannula 20.

In some embodiments, the cannula 20 further comprises a channel 25 for the slidable insertion a viewing device, such as an endoscope. In some embodiments, the channel 25 is located below the horizontal blade guidance tracks 24. In some embodiments, the channel 25 and the horizontal blade guidance tracks 24 form a single contiguous lumen that is also contiguous with the slot 21. In other embodiments, there is a layer of material molded as part of the cannula 20 between the channel 25 and the horizontal blade guidance tracks 24, such that the lumen of the channel 25 is physically separate from the lumen contiguous with the slot 21 and comprising the horizontal blade guidance tracks 24.

In some embodiments, the proximal end 22 of the cannula 20 is adapted to engage with a connection point 31 on the front end of the case 30. The attachment can be by any means known in the art, such as, but not limited to, adhesives, tabs, welds, laser welds, locking mechanism, twist-lock, or friction fitting. In order to provide a stable platform for endoscopic surgical procedures using the device, the attachment of the cannula 20 to the case 30 is such that, when assembled, the cannula 20 can not move in relation to the case 30.

In some embodiments, the case 30 of the device comprises two halves 32, 33 that mate to one another to form a single case 30. In some embodiments, the case 30 may be formed as a single piece or comprise three or more pieces.

The interior of the case 30 comprises a guidance slot 34 on each side of the case such that the two guidance slots 34 are horizontally opposed to one another. The tabs 14 of the blade 10 are slidably associated with the horizontally opposed guidance slots 34. In some embodiments, the height of the horizontally opposed guidance slots 34 is parallel to with respect to a horizontal plane that would bisect the cannula 20 into two equal halves. In other embodiments, the height of the horizontally opposed guidance slots 34 is at an angle with respect to a horizontal plane that would bisect the cannula 20 into two equal halves, such that the end of the horizontally opposed guidance slots 34 distal to the cannula 20 is lower in the device with respect to the end of the horizontally opposed guidance slots 34 proximal to the cannula 20.

When the tabs 14 are drawn back in the horizontally opposed guidance slots 34, the cutting component 12 is contained within the proximal end 22 of the slot 21 of the cannula 20 and the cutting surface 13 does not protrude outside the device. As the tabs 14 are advanced in the horizontally opposed guidance slots 34 toward the connection point 31 with the cannula 20, the cutting component 12 slides in the distal direction of the slot 21 of the cannula 20 and moves the cutting surface toward the distal end 23 of the cannula 20.

In some embodiments, the device comprises a paddle 40 that contacts the blade 10 behind or between the tabs 14. The paddle 40 comprises a grip area 41 that protrudes out of the case 30 through a slot 35. The blade 10 is slidably advanced along the horizontally opposed guidance slots 34 by advancing the paddle 40 towards the cannula 20 through the slot 35, causing the contact area 42 of the paddle 40 to push against the pushing component 11 of the blade 10.

In some embodiments, the paddle 40 comprises at least one arm that extends forward of the tabs 14 that allows the paddle 40 to capture the tab 14 and pull the blade 10 back to a withdrawn position following completion of an endoscopic surgical procedure.

In some embodiments, the paddle 40 is secured in the device by a retaining ring 50. The retaining ring 50 comprises wings 51 that slidably interact with the horizontally opposed guidance slots 34 of the case 30. The retaining ring 50 further comprises an attachment ring 52 that connects to the connection region 43 of the paddle 40. The connection region 43 of the paddle 40 may comprise any means known in the art for connecting the paddle 40 to the retaining ring 50. For example, the connection region 43 may comprise tabs that extend through and entrap the attachment ring 52. In some embodiments, the connection between the connection region 43 and the attachment ring 52 allows the paddle 40 to rotate side-to-side in relation to the retaining ring and the blade 10.

In some embodiments, the paddle 40 can be retained, parked or locked in a position fully distal to the cannula 20 by rotating the grip area 41 of the paddle 40 into, for example, a notch 36 in the case 30.

In some embodiments, the case 30 further comprises an opening 39 at the end distal to the cannula 20 through which an endoscope can be inserted. The endoscope is fed through the opening 39 and under the blade 10 to be inserted into the channel 25 of the catheter 20. This allows direct visualization of the surgical site and the surrounding tissue before, during and after performing an endoscopic surgical procedure with the present device.

Another aspect of the present application relates to a slotted clear cannula having a closed end such that the cannula can be inserted into an incision or natural body opening and into a passage through body tissue without the use of a device, such as an obturator, filling the lumen of the cannula for insertion. In particular embodiments, the closed end of the cannula is tapered, but is sufficiently blunted such that it does not damage bodily tissues as it is advanced though an incision and channel through bodily tissue, or through a natural body opening. In another particular embodiment, the slot is contiguous with the open end of the cannula opposite the closed end.

Rotationally Operated Device

Figure 2:
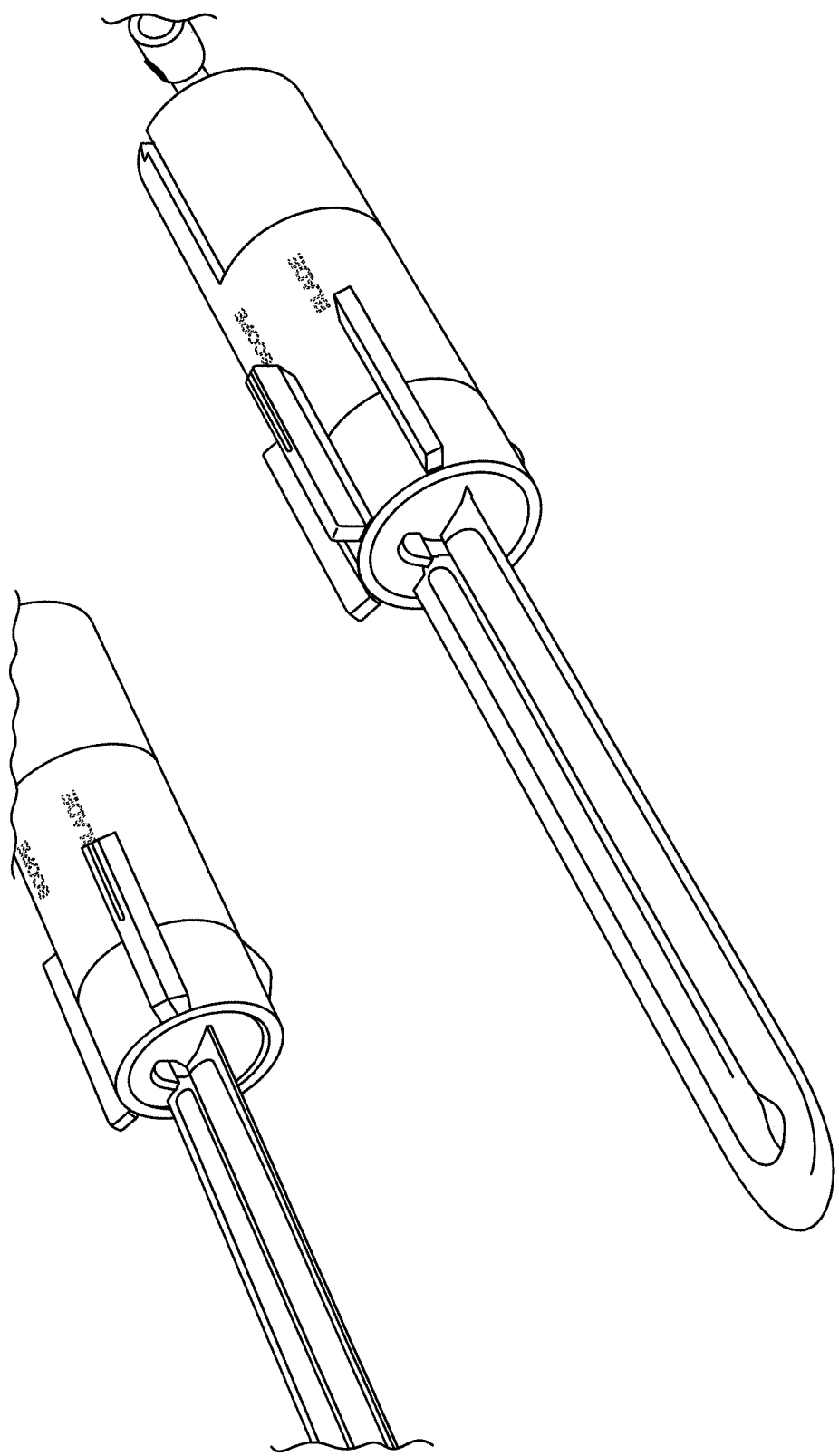
FIG. 2 is a perspective view of another embodiment of the device of the present application.
Figure 3:
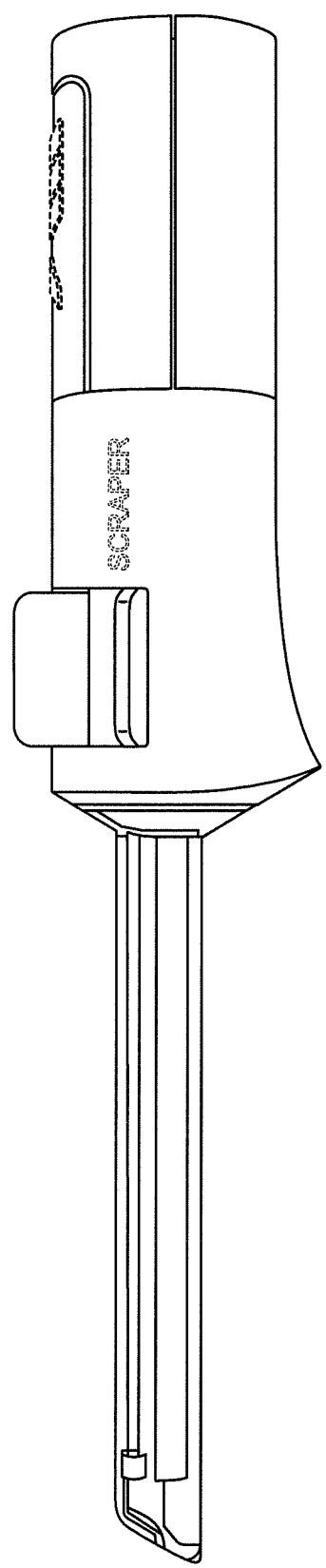
FIG. 3 is a perspective view of another embodiment of the device of the present application.

FIGS. 2 and 3 show embodiments of the present application wherein the device comprises a rotational switch for selecting the tool to advance into the cannula. FIG. 2 shows an embodiment comprising selection positions for advancing the endoscope alone into the cannula and for advancing a blade along the endoscope into the cannula. FIG. 3 shows an alternate embodiment, wherein the device further comprises a selectable scraper that can be advanced along the endoscope into the cannula.

Figure 4:
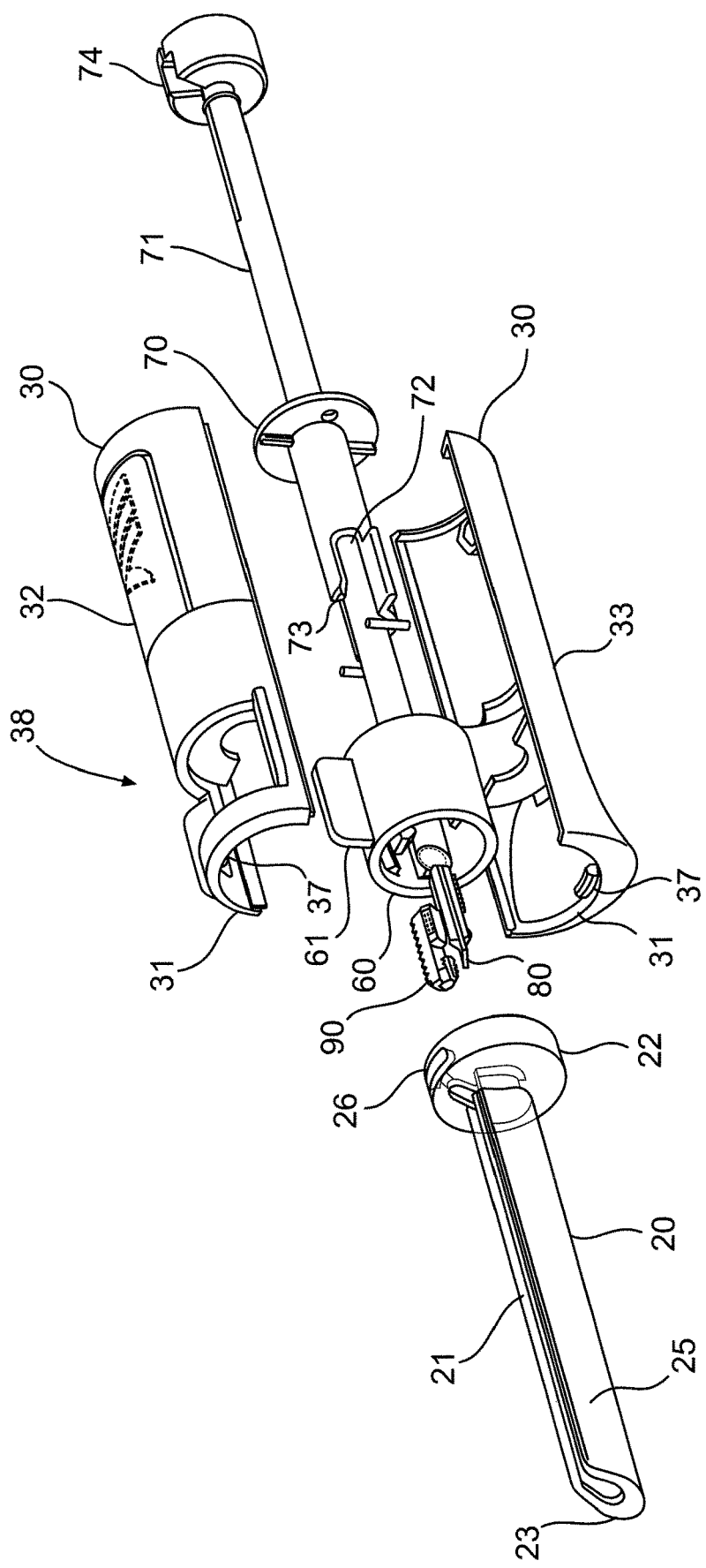
FIG. 4 is an exploded view of the embodiment of the device depicted in FIG. 3.

FIG. 4 depicts an exploded view of the present device of FIG. 3. The case 30 is cylindrical in shape and is comprised of two halves 32,33. The proximal end 22 of the cannula 20 is adapted to engage with a connection point 31 on the front end of the case 30. In some embodiments, the proximal end 22 of the cannula 20 comprises depressions 26 that engage with tabs (or pins) 37 at the connection point 31 on the front end of the case 30. As used herein, the term "depression" is understood to include, but is not limited to, depressions that do not penetrate completely through the material of the cannula, as well as holes or slots that penetrate completely through the material of the cannula.

The case 30 further includes an opening 38 that can be located in either half 32,33 of the case. in some embodiments, the opening 38 may span the junction between the halves 32,33 of the case 30, being located partially in each half. The opening 38 is located adjacent to an internal revolver 60 that comprises a selector switch 61 that protrudes through the opening 38.

Still referring to FIG. 4, the device further comprises an inner sleeve 70 that encircles a guidance tube 71. The inner sleeve 70 comprises notches 72,73 at its distal end that provide pre-deployment resting places for the blade 80 and the scraper 90. The inner sleeve 70 works in concert with the revolver 60 in order to bring the blade 80 or scraper 90 into the proper orientation for deployment into the slot 21 of the cannula 20. The guidance tube 71 provides a path for deploying an endoscope through the device and into the cannula 20. The guidance tube 71 also provides, at its distal end, a mounting point 78 (shown in FIG. 8A) that the blade 80 or scraper 90 is rotated onto for deployment. Using the pusher ring 74, the guidance tube 71 is advanced along the deployed endoscope into the cannula 20, thereby deploying the blade 80 or scraper 90 into the slot 21 of the cannula 20.

Figure 5:
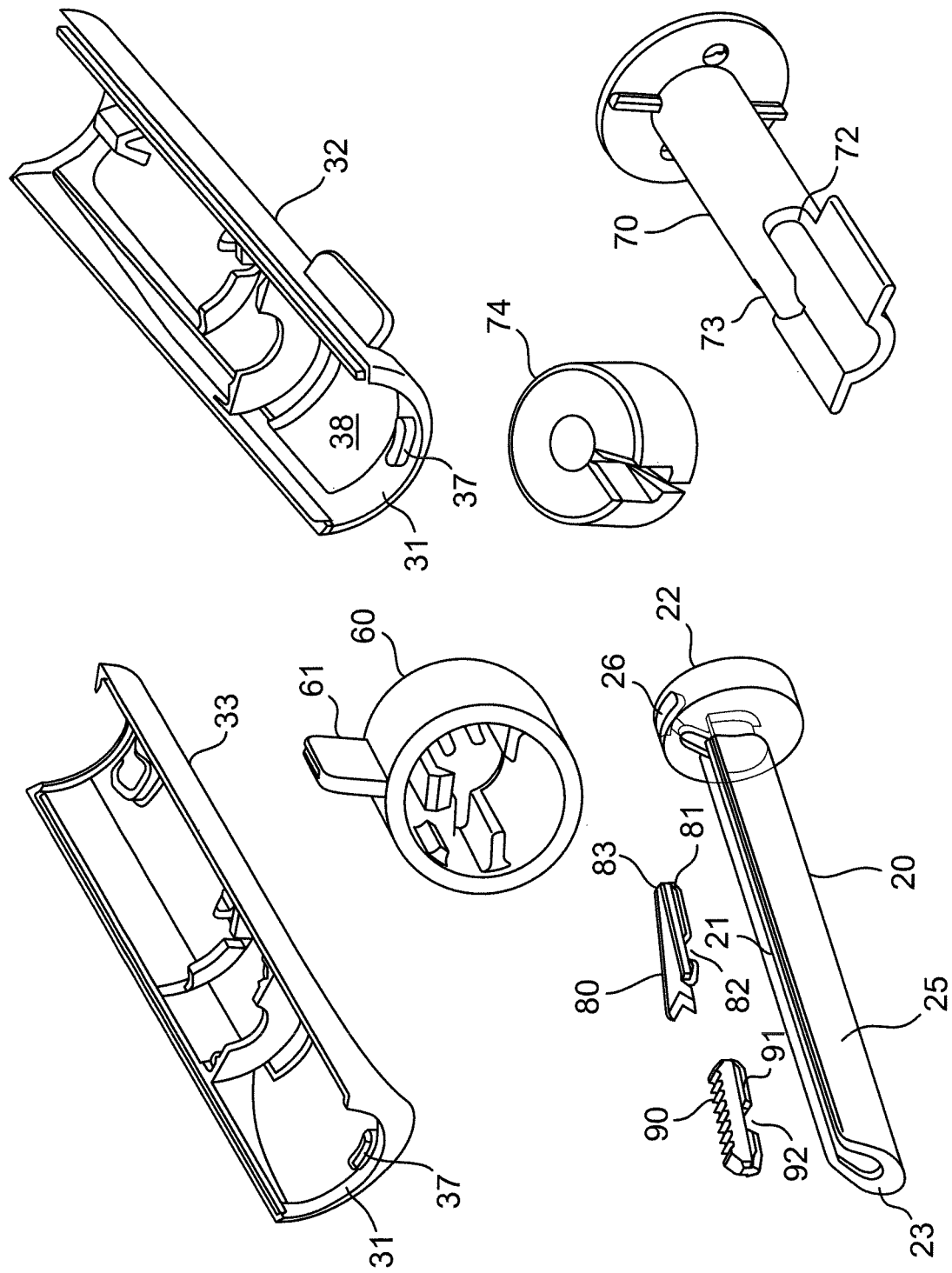
FIG. 5 shows individual components of the device depicted in FIG. 3.

Now turning to FIG. 5, a number of components of the device depicted in FIG. 3 are shown separately from one another. It is understood that the individual elements of the device are not limited to the exact configuration depicted in the figures herein. Any design of particular elements of the device that can be envisioned by one of ordinary skill in the art to perform the same function in concert with other elements is included as part of the present disclosure.

Also in FIG. 5, the blade 80 comprises a base 81 that allows the blade 80 to be secure in its pre-deployment notch 72 of the inner sleeve 70. When the blade 80 is rotated into deployment orientation, the notch 82 in the base 81 engages the mounting point 78 (shown in FIG. 8A) on the distal end of the guidance tube 71. As the blade 80 is distally deployed into the slot 21 of the cannula 20, the base 81 retains the blade 80 in the device by underlapping the sides of the slot 21 within the channel 25 of the cannula 20. Additionally, to prevent any unwanted side-to-side motion of the blade 80 as it is deployed distally through the slot 21 of the cannula 20, in some embodiments the blade further comprises a ridge 83 that fills the slot side-to-side. Additionally, the engagement of the notch 82 with the mounting point 78 allows the blade 80 to be safely retracted back into the case 30 following usage of the blade 80 for an endoscopic surgical procedure.

Still referring to FIG. 5, the scraper 90 comprises a base 91 that allows the scraper 90 to be secure in its pre-deployment notch 73 of the inner sleeve 70. When the scraper 90 is rotated into deployment orientation, the notch 92 in the base 91 engages the mounting point 78 (shown in FIG. 8A) on the distal end of the guidance tube 71. As the scraper 90 is distally deployed into the slot 21 of the cannula 20, the base 91 retains the scraper 90 in the device by underlapping the sides of the slot 21 within the channel 25 of the cannula 20. Additionally, the engagement of the notch 92 with the mounting point 78 allows the scraper 90 to be safely retracted back into the case 30 following usage of the scraper 90 for an endoscopic surgical procedure.

Figure 6:
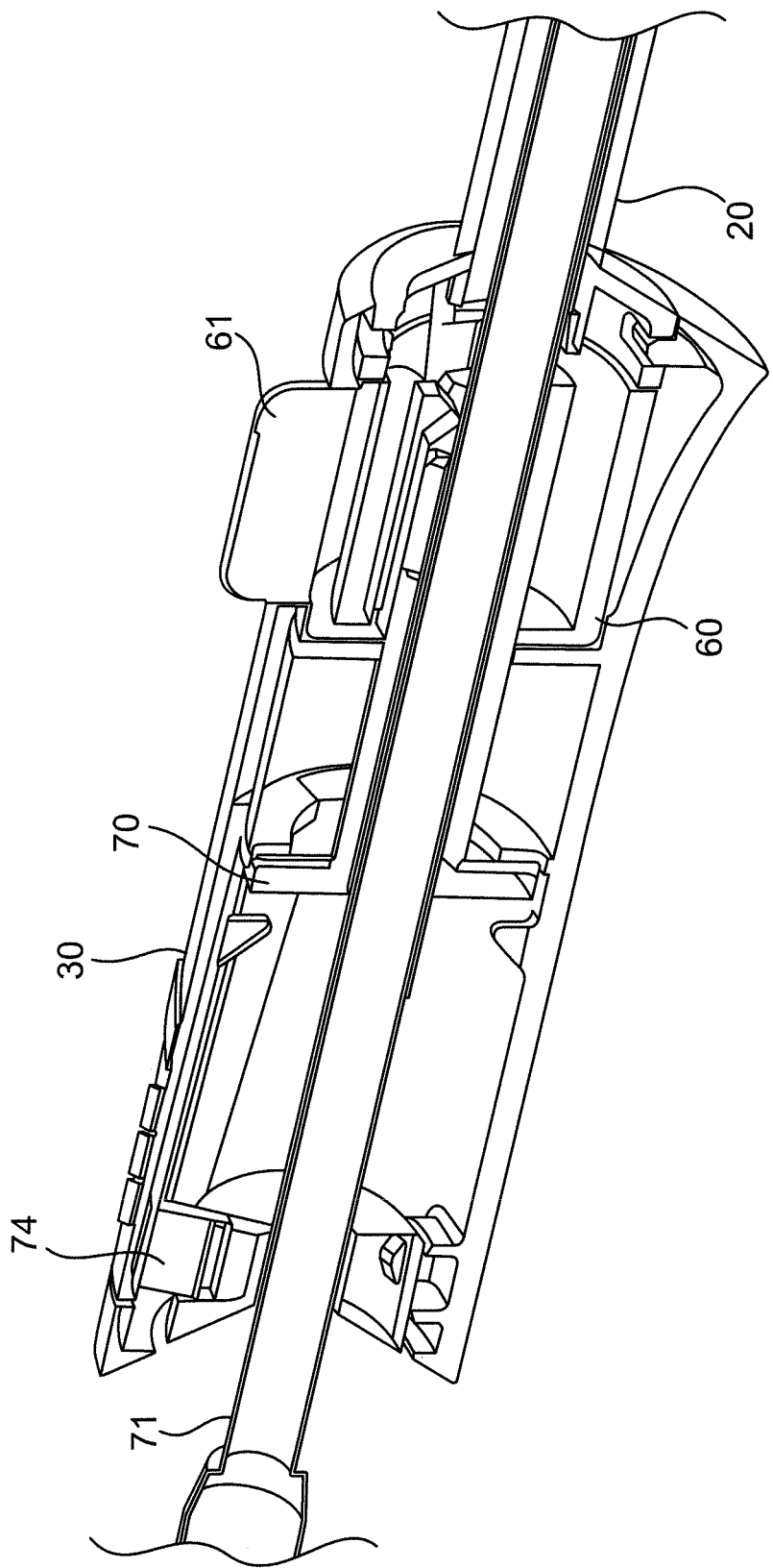
FIG. 6 is a cutaway view of the embodiment of the device depicted in FIG. 3.

Turning to FIG. 6, a cutaway drawing is shown that depicts the passage of the guidance tube 71 through the inner sleeve 70 and into the cannula 20.

Figure 7:
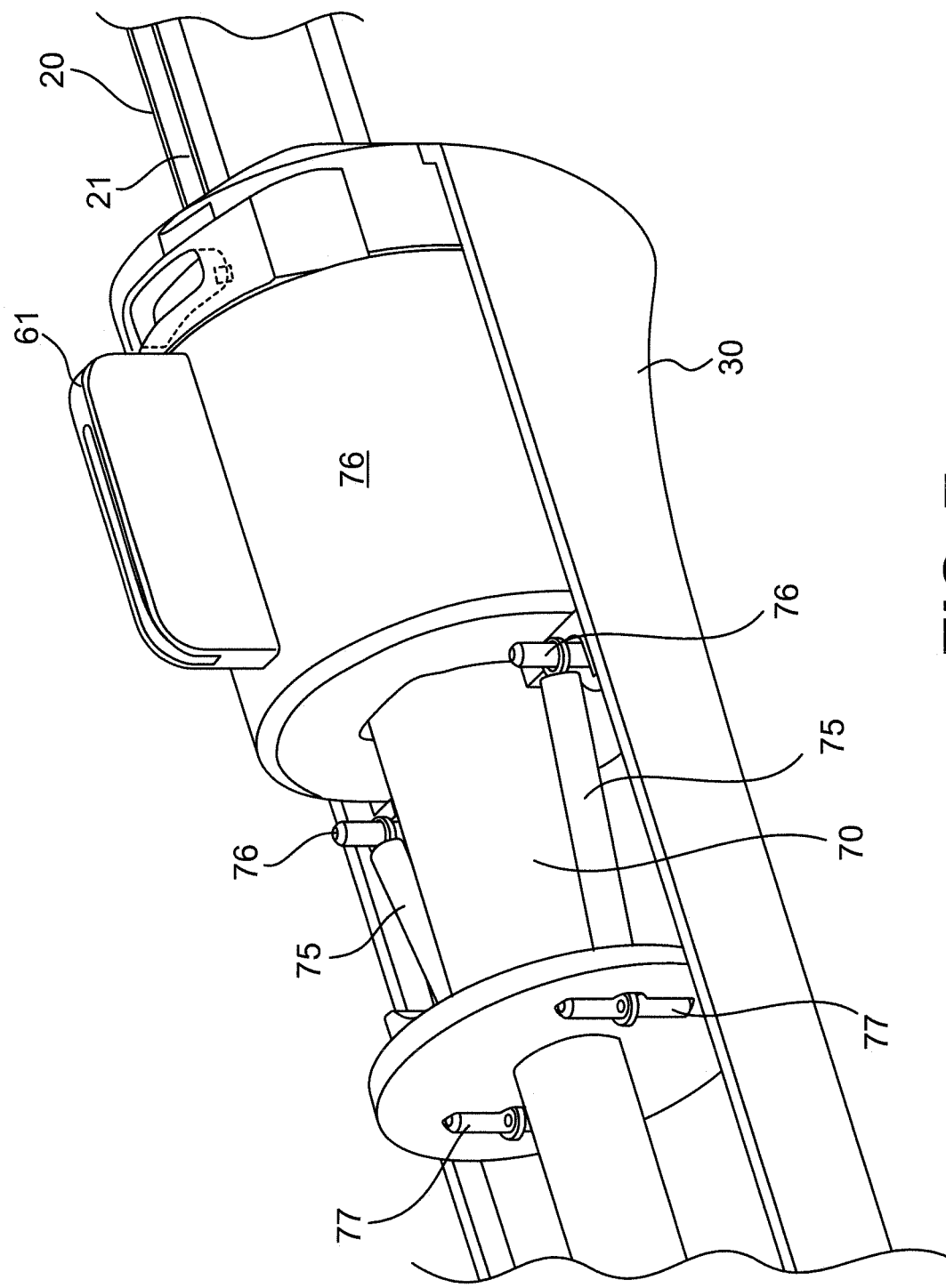
FIG. 7 is an exploded view of individual components of the device depicted in FIG. 3.

FIG. 7 is a cutaway drawing showing an exemplary relationship of the inner sleeve 70 to the revolver 60 of the device. The inner sleeve 70 extends into the revolver 60 and the pre-deployment slots 72,73 holding the blade 80 and the scraper 90 are located inside the revolver 60. In an exemplary configuration, springs 75 are attached to pins 76 located on the revolver 60. The springs 75 extend to pins 77 that secure the opposite end of the springs to the inner sleeve 70. The springs 75 auto center the revolver 60 within the device. Upon rotation of the revolver 60, the springs 75 activate detents for the three modes: 1) deployment of the endoscope, 2) orientation of the scraper 90 in deployment configuration, and 3) orientation of the blade 80 in deployment configuration.

Figure 8:
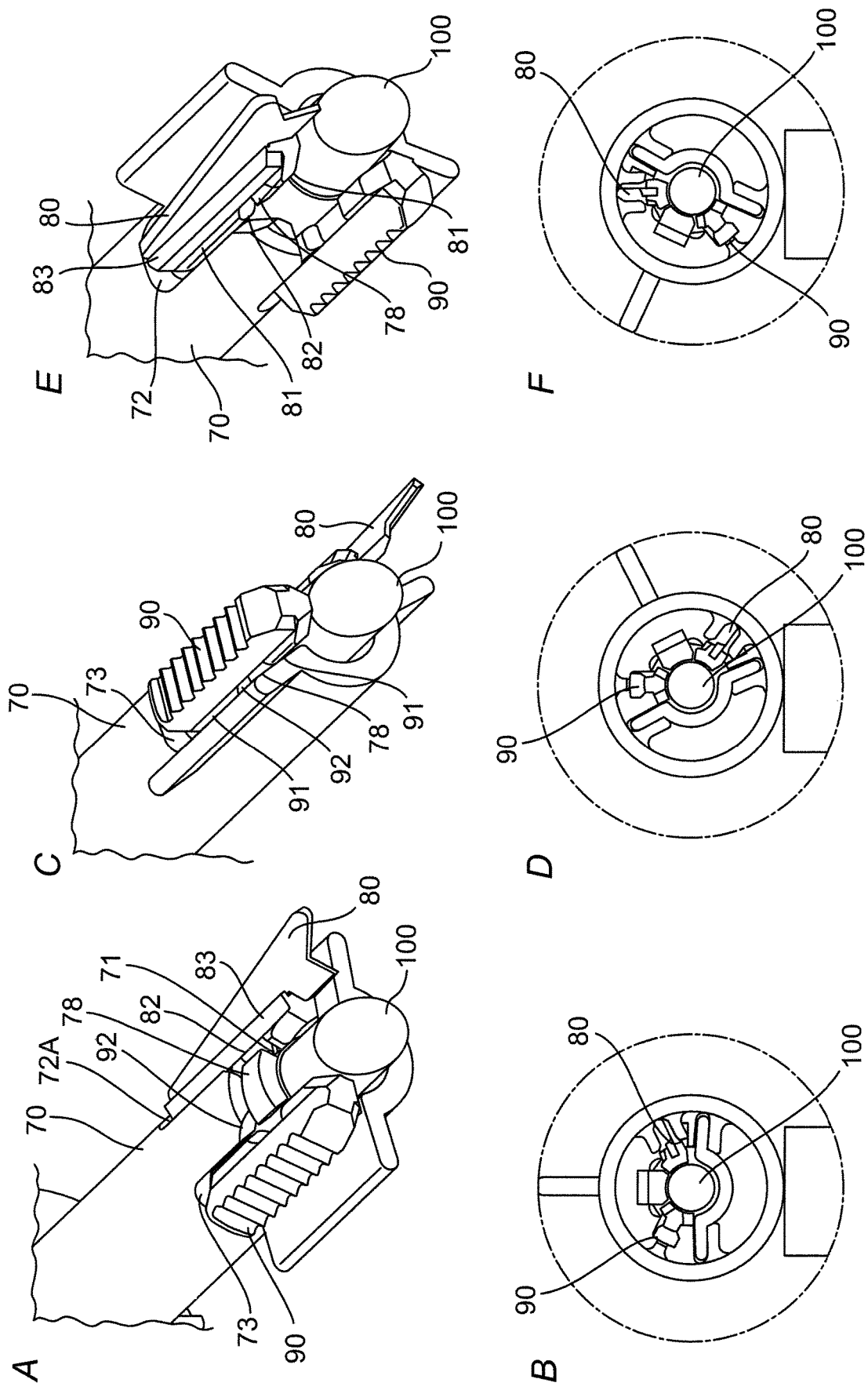
FIGS. 8A-F show the orientation of the internal components in side view (A,C,E) and end view (B,D,F) of the device of FIG. 3 for the advancement of an endoscope alone (A,B), an endoscope with a scraper (C,D) or an endoscope with a blade (E,F).

FIGS. 8A-F show the rotation of the inner sleeve corresponding to the three modes. FIGS. 8A, viewing from above, and 8B, viewing from a distal position, are a depiction of the first mode, wherein the an endoscope 100 can be advanced through the guidance tube 71 into the cannula 20, without the deployment of the scraper 90 or the blade 80. The mounting point 78 is not engaged with either the blade 80 or the scraper 90, therefore preventing the deployment of either tool in this mode.

FIGS. 8C, viewing from above, and 8D, viewing from a distal position, are a depiction of the second mode, wherein the revolver 60 has been turned to select the scraper 90. the inner sleeve 70 is rotated in concert with the revolver 60 to bring the scraper 90 into deployment orientation. The slot 92 in the base 91 of the scraper 90 is rotated to engage the mounting point 78 on the guiding tube (hidden). The guiding tube is then pushed distally into the cannula 20 with the scraper 90 protruding through the slot 21. Following use of the scraper 90, the guiding tube is retracted from the cannula 20 and the revolver 60 is returned to the first mode, restoring the scraper to its pre-deployment configuration of FIGS. 8A-B.

FIGS. 8E, viewing from above, and 8F, viewing from a distal position, are a depiction of the third mode, wherein the revolver 60 has been turned to select the blade 80. The inner sleeve 70 is rotated in concert with the revolver 60 to bring the blade 80 into deployment orientation. The slot 82 in the base 81 of the blade 80 is rotated to engage the mounting point 78 on the guiding tube (hidden). The guiding tube is then pushed distally into the cannula 20 with the blade 80 protruding through the slot 21. Following use of the blade 80, the guiding tube is retracted from the cannula 20 and the revolver 60 is returned to the first mode, restoring the blade 80 to its pre-deployment configuration of FIGS. 8A-B.

Kit

Another aspect of the present application relates to an instrument kit for implementing an endoscopic surgical procedure. The instrument kit contains an endoscopic surgical device comprising a slotted clear cannula, a blade and a case, wherein the cannula is attached to the case, and further wherein the blade is enclosed in the case and is slidable into the cannula.

In some embodiments, the endoscopic surgical device comprises a slotted clear cannula, a scraper, a blade and a case, wherein, the cannula is attached to the case, in a pre-deployment configuration the scraper and the blade are enclosed in the case, the blade and scraper are individually selectable for deployment orientation, and in deployment orientation the blade or scraper are slidable into the cannula.

In some embodiments, the instrument kit comprises components and implements useful for endoscopic procedures.

In one embodiment, the instrument kit further includes an endoscope sized for insertion into the slotted clear cannula for direct visualization of an operative site.

In another embodiment, the instrument kit further includes a scalpel.

In another embodiment, the instrument kit further includes an elevator.

In another embodiment, the instrument kit further includes a depth gauge mountable to a leading end of the endoscope.

In another embodiment, the instrument kit further includes a stop device mountable on or in the cannula to prevent excessive penetration at a surgical site by the cutting instrument.

In another embodiment, the instrument kit further includes a curved dissector.

Method for Endoscopic Surgery

Another aspect of the present application relates to a method for uniportal endoscopic surgery. Uniportal endoscopic surgery allows the practitioner to visualize a target tissue and its surrounding tissues as well as perform a surgical procedure through a single entry portal. In some instances, the entry portal may be a natural opening, while in other instances the entry portal is an incision. In the case of an incision, generally only a single small incision must be made. In particular embodiments, the incision is less than or equal to about 2 cm in length. In more particular embodiments, the incision is less than or equal to about 1.5 cm in length. In still more particular embodiments, the incision is less than or equal to about 1 cm in length. The single small incision allows the patient to recover more quickly and begin therapy and/or resume normal activity as tolerated sooner.

The uniportal endoscopic surgical procedure described herein can be used to implement a number of different surgical procedures including, but not limited to, trigger finger release, carpal tunnel release, cubital tunnel release, release of compressions of the radial, median or ulnar nerves, plantar fascia release, lateral release for patella realignment, release of the extensor tendons, release of the posterior and other compartments of the leg, and forearm fascial release.

One embodiment of the present application relates to a method for a performing a uniportal endoscopic surgical procedure a target tissue in a subject. Generally, following the establishment of an entry portal, in some embodiments a blunt instrument, such as an elevator is inserted through the portal to establish an opening in the underlying tissue between the portal and the target tissue.

In one embodiment, an endoscopic surgical device comprising a slotted clear cannula, a blade and a case, wherein the cannula is attached to the case, and further wherein the blade is enclosed in the case and is slidable into the cannula, is inserted into the entry portal and extended through to the target tissue.

In some embodiments, the endoscopic surgical device comprises a slotted clear cannula, a scraper, a blade and a case, wherein, the cannula is attached to the case, in a pre-deployment configuration the scraper and the blade are enclosed in the case, the blade and scraper are individually selectable for deployment orientation, and in deployment orientation the blade or scraper are slidable into the cannula.

An endoscope is inserted through the case and into the cannula to view the target tissue and the surrounding tissues, assuring that the slot of the cannula is in proper orientation to the target tissue.

The paddle of the endoscopic surgical device is released from its locked or parked position and advanced along the slot in the case so that the knife is advanced further through the cannula so that the blade moves in contact with the target tissue through the slot, operatively engaging the target tissue with the blade. The blade is further advanced through the cannula to divide the target tissue.

In one particular embodiment, the operative procedure is trigger finger release.

In another particular embodiment, the establishing an entry portal comprises making an incision.

In another particular embodiment, the target tissue is the A1 pulley.

The present invention is further illustrated by the following examples which should not be construed as limiting. The contents of all references, patents and published patent applications cited throughout this application, as well as the Figures and Tables, are incorporated herein by reference.

Example 1

Uniportal Endoscopic Trigger Release

In a patient presenting with trigger finger of the middle or ring finger, a 1 cm incision is made just proximal to the A1 pulley on the distal palmar crease proximate to the affected digit.

An elevator is introduced into the incision and used to create a plane superficial to the flexor tendon sheath. The elevator is withdrawn.

The cannula portion of an endoscopic surgical device comprising a slotted clear cannula, a scraper, a blade and a case, wherein the cannula is attached to the case, and further wherein the scraper and blade are enclosed in the case, are individually selectable for deployment and are slidable into the cannula is introduced into the incision and advanced through the plane created by the elevator. The slot of the cannula is oriented facing the flexor tendon sheath.

The revolver of the device is set to allow the advancement of the endoscope without the deployment of the blade and scraper. The endoscope is introduced through the guidance tube in the case of the endoscopic surgical device and into the cannula and advanced to visualize the A1 pulley and A2 pulley.

In the event that the tenosynovium obscures visualization of the tendon, the revolver of the device is turned to select deployment orientation of the scraper. The guiding tube is advanced along the endoscope into the cannula and the scraper protrudes through the slot of the cannula. The tenosynovium is removed with the scraper and the guiding tube is retracted, bringing the scraper back into the case of the device. The revolver of the device is rotated to restore the scraper back to its pre-deployment configuration in the device.

The tendon is again visualized with the endoscope. The revolver of the device is turned to select deployment orientation of the blade. The guiding tube is advanced along the endoscope into the cannula and the blade protrudes through the slot of the cannula. The blade is advanced into contact with the A1 pulley. The blade is further pushed forward, dividing the A1 pulley. The guiding tube is retracted, bringing the blade back into the case of the device. The revolver of the device is rotated to restore the blade back to its pre-deployment configuration in the device.

The cut edges of the A1 pulley and the underlying flexor tendon are visualized through the endoscope.

While visualizing the tendon, release of the tendon is confirmed by passive manipulation of the digit through its range of motion.

The absence of triggering is confirmed by having the subject flex and extend the affected digit.

The endoscope is withdrawn and the cannula is removed from the incision.

The wound is closed and a soft bandage is applied.

The patient is encouraged to begin early finger motion following surgery and to resume daily activities as tolerated.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the components and steps in any sequence which is effective to meet the objectives there intended, unless the context specifically indicates the contrary.

What is claimed is:

1. An endoscopic surgical device comprising: a slotted clear cannula comprising a longitudinal slot along its top, the cannula comprising a proximal cannula end and an open or closed distal cannula end, a blade comprising a vertically-oriented cutting surface, wherein the longitudinal slot of the cannula and the vertically-oriented cutting surface of the blade together define a vertical plane; a horizontally-oriented pusher component attached to and extending proximally from the blade; and a case proximal to the cannula, the case having a proximal case end and a distal case end, wherein: the case internally comprising sloping, horizontally opposed guidance slots, the pusher component comprises tabs situated at a proximal end thereof that are slidably associated with the sloping, horizontally oriented guidance slots, the proximal cannula end is attached to the distal case end, the blade protrudes through the slot in the cannula when deployed in a vertical direction substantially aligned with the vertical plane, the pusher component is enclosed by the case, and the proximal end of the pusher component is enclosed by the case, and the proximal case end acts as a stop to prevent the proximal end of the pusher component from extending outwardly from the proximal case end.

2. The endoscopic surgical device of claim 1, wherein the distal cannula end is closed.

3. The endoscopic surgical device of claim 2, wherein the closed end of the cannula is tapered.

4. The endoscopic surgical device of claim 1, wherein the case comprises an opening proximal to the cannula.

5. A method for a performing a uniportal endoscopic surgical procedure on a target tissue in a subject in need thereof, comprising:
    establishing an entry portal in the subject,
    inserting into the entry portal the cannula of the endoscopic surgical device of claim 1, and
    extending the cannula through the entry portal to the target tissue.

6. The method of claim 5, further comprising inserting an endoscope through an opening in the case and into a channel of the cannula.

7. The method of claim 5, further comprising advancing the blade through the cannula to divide the target tissue.

8. The method of claim 5, wherein the uniportal endoscopic surgical procedure is selected from the group consisting of trigger finger release, carpal tunnel release, cubital tunnel release, plantar fascia release, lateral release for patella realignment, release of the extensor tendons, release of the posterior or other compartments of the leg, and forearm fascial release.

9. The method of claim 5, wherein the target tissue is selected from the group consisting of the A1 pulley, carpal tunnel, cubital tunnel and Guyon's tunnel.

* * * * *